United States Patent [19]  [11] 3,935,246
Bernauer et al.  [45] Jan. 27, 1976

[54] NAPHTHOQUINONES
[75] Inventors: Karl Bernauer, Allschwil; Erika Böhni, Basel, both of Switzerland; Janos Borgulya, Upper Montclair, N.J.
[73] Assignee: Hoffmann-La Roche Inc., Nutley, N.J.
[22] Filed: Dec. 18, 1974
[21] Appl. No.: 533,902

[30] Foreign Application Priority Data
Jan. 10, 1974   Switzerland............................ 282/74

[52] U.S. Cl.......... 260/396 R; 260/566 R; 260/571; 424/330
[51] Int. Cl.²........................................ C07C 97/22
[58] Field of Search ................................ 260/396 R

[56] References Cited
UNITED STATES PATENTS
3,114,755  12/1963  Covey ............................... 260/396 R
3,682,980   8/1972  Braid et al. ........................ 260/396 R
3,729,492   4/1973  Bernauer et al. ................... 260/396 R OTHER PUBLICATIONS
Chem. Abstracts, 70:57493n.
Chem. Abstracts, 71:2032b.
Chem. Abstracts, 52:18413e.
Chem. Abstracts, 50:3358h.

*Primary Examiner*—Vivian Garner
*Attorney, Agent, or Firm*—Samuel L. Welt; Jon S. Saxe; Gerald S. Rosen

[57]  ABSTRACT

Compounds represented by the formula

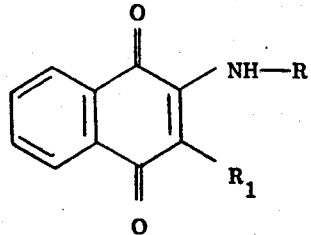

wherein
  R is a cyclopentyl or cycloheptyl and
  $R_1$ is a hydrogen, halogen or lower alkoxy, processes for their production and novel intermediates as well as therapeutic preparations containing the compounds as the active ingredient for amoebicidal or bacteriostatic treatment are disclosed.

3 Claims, No Drawings

NAPHTHOQUINONES

DESCRIPTION OF THE INVENTION

The present invention relates to amoebicidal and bacteriostatic naphthoquinone derivatives, novel intermediates therefor, processes for the preparation thereof and pharmaceutical preparations containing the naphthoquinone derivatives as the active compound.

The naphthoquinone derivatives of this invention are represented by the following formula

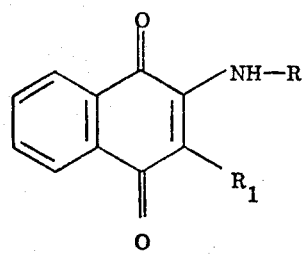

I wherein
R is a cyclopentyl or cycloheptyl and
$R_1$ is a hydrogen, halogen or lower alkoxy.

As used herein the term "lower alkoxy" means a straight-chain or branched-chain lower alkyl ether group containing from 1 to 4 carbon atoms (e.g., methoxy, ethoxy, propoxy, butoxy and the like). The term "halogen" means fluorine, chlorine, bromine or iodine, with chlorine and bromine being preferred and chlorine most preferred.

The compounds of formula I possess amoebicidal and bacteriostatic activity, especially against gram-negative bacteria such as, for example, *Escherichia coli*, *Shigella sonnei* and/or *Shigella flexneri*. They may accordingly be used for the treatment of illnesses such as dysentery and dyspepsia which are caused by these organisms.

The compounds are relatively non-toxic when compared to their curative doses, thus, 2-chloro-3-cyclopentylamino-1,4-naphthoquinone and 2-chloro-3-cycloheptylamino-1,4-naphthoquinone have a LD (lethal dose) 50 of greater than 5000 mg./kg. p.o. in the mouse and a CD 50 of less than 50 mg./kg. p.o. against *Escherichia coli*, *Shigella flexneri* and *Shigella sonnei*.

The CD (curative dose) 50 values were determined according to the following method:

Groups each containing five mice are de-wormed over a period of four days. At the same time, the mice are put on a carbohydrate-rich diet (popcorn). No food is administered on the fifth day. From the sixth day up to the end of the experiment the mice are given drinking water which contains, per liter, 4 g. of dihydrostreptomycin, 100 mg. of erythromycin and 400,000 units of mycostatin. On the sixth day they are given more popcorn. On the seventh day no food is given. On the eight day no food is again given and the mice are infected orally with 100 million streptomycin-, erythromycin- and mycostatin-resistant germs of *Shigella sonnei*, *Shigella flexneri* or *Escherichia coli*. From the ninth day up to the end of the experiment the mice are given popcorn and, 24 hours after the oral infection, the naphthoquinone derivative to be tested is administered for the first time. The naphthoquinone derivative is administered three times in intervals of 24 hours in the case of *Shigella sonnei* and *Escherichia coli* and five times in intervals of 24 hours in the case of *Shigella flexneri*. The mice infected with *Shigella flexneri* are killed one day after the last administration and the mice infected with *Shigella sonnei* or *Escherichia coli* are killed three days after the last administration.

A portion of the colon together with the content thereof (ca 200 mg.) is isolated and homogenized. Six different dilutions (1/10,000; 1/50,000; 1/100,000; 1/500,000; 1/1,000,000; 1/2,000,000) are prepared therefrom.

One drop of each dilution is streaked on an agar plate. After incubation for 48 hours, the number of colonies is counted and, with the corresponding dilutions, the germ count per gram of colon is calculated for each mouse. By comparison of the individual germ counts of 5 mice with the average germ counts of 5 untreated mice, the percentage germ reduction in each mouse is calculated. The results are given in CD 50 values.

The compounds of formula I can be used as medicaments in the form of therapeutically useful pharmaceutical preparations which contain them as the active ingredient in association with a compatible pharmaceutical carrier. This carrier can be a non-toxic pharmaceutically acceptable organic or inorganic carrier material suitable for enteral or parenteral administration such as water, gelatin, lactose, starch, magnesium stearate, talc, vegetable oils, gum arabic, polyalkylenegylcols, petroleum jelly and the like. The pharmaceutical preparations can be made up in a solid form, e.g., as tablets, dragees, suppositories or capsules, or in a liquid form, e.g., as solutions, suspensions or emulsions. The pharmaceutical preparations may be sterilized and/or may contain adjuvants such as preserving, stabilizing, wetting or emulsifying agents, salts for varying the osmotic pressure or buffers. The pharmaceutical preparations may also contain other therapeutically valuable substances. The amount of active compound in any particular formulation effective for the treatment of diseases caused by amoeba or bacteria depends upon the formulation, dosage regimen and patient being treated. This can be determined by the clinician.

The compounds of formula I are preferably administered orally, i.e., in dosage forms which are customary for oral administration such as, for example, dragees, tablets, capsules and the like. Tablets which contain about 100 mg. 200 mg. or 250 mg. of active compound are especially preferred. Daily dosages of from 100 mg. to about 1000 mg., corresponding to from 1.4 mg./kg./day to about 14 mg./kg./day, can be administered in several individual doses or other regimens can be used depending on the judgment of the treating clinician.

The naphthoquinone derivatives represented by formula I can be prepared as follows:

a. Reacting a compound represented by the formula

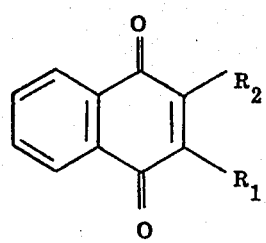

II wherein
R₁ has the significance given earlier and
R₂ is hydrogen or a leaving atom or group,
with cyclopentylamine or cycloheptylamine.

The reaction of a compound of formula II with cyclopentylamine or cycloheptylamine is conveniently carried out in an organic solvent which is inert under the reaction conditions, for example, an alcohol, e.g., methanol, ethanol or the like, an aliphatic hydrocarbon, a halogenated aliphatic hydrocarbon. e.g., methylene chloride, an aromatic hydrocarbon, e.g., benzene or nitrobenzene, dioxane, tetrahydrofuran, dimethylformamide or the like.

The reaction can be carried out at a temperature of from about room temperature to the reflux temperature of the reaction mixture. The reaction is preferably carried out at the reflux temperature.

An excess of cyclopentylamine or cycloheptylamine is conveniently used in the reaction in order to bind the acid which may be liberated. However, for this purpose there may also be used as organic base which is inert under the reaction conditions such as, for example, a tertiary organic amine, e.g., triethylamine, pyridine or the like.

b. Oxidizing a compound represented by the formula

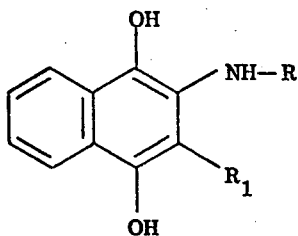

III

, wherein R and R₁ have the significance given earlier, and, if desired, subsequently replacing in the final product of formula I a hydrogen or a non-chlorine halogen denoted by R₁ by chlorine, using conventional procedures.

The oxidation of a compound of formula III can be carried out in a conventional manner, for example, by letting the reaction mixture stand in air, by passing air or oxygen through the reaction mixture, by shaking the reaction mixture with dilute hydrogen peroxide or by treatment with ferric salts or the like.

The conversion of a naphthoquinone derivative of formula I in which R₁ is hydrogen into a naphthoquinone derivative of formula I in which R₁ is chlorine can conveniently be carried out by passing chlorine gas through a solution of a naphthoquinone derivative of formula I in which R₁ is hydrogen. In the case where R₁ is a non-chlorine halogen, the halogen can be replaced by chlorine by heating in a suitable solvent with, for example, lithium chloride. The heating is conveniently carried out at a temperature of about 50°C. to 150°C., preferably to about 80°C. to 120°C.

The term "leaving atom or group" as used herein means a lower acyloxy, e.g., acetoxy, propionyloxy and the like, a lower alkoxy, e.g., methoxy, ethoxy and the like, an aryloxy, e.g., phenoxy, an aralkoxy, e.g., benzyloxy and the like, an arylsulphonyloxy, e.g., tosyloxy, a lower alkylsulphonyloxy, e.g., mesyloxy, an arylthio, an aralkylthio, hydroxy or halogen atom or the like. As used herein "aryl" means a monocyclic aryl, e.g., benzene, "alkyl" when used in connection with other groups means straight and branched chain lower alkyl of 1–4 carbon atoms.

The compounds of formula II are well known compounds.

The compounds of formula III are novel and are included in the present invention. The preferred compounds of formula III are those wherein R₁ is chlorine or bromine, most preferably chlorine.

The compounds of formula III can be prepared, for example, by reducing a compound of formula I. The reduction is preferably carried out catalytically, e.g., using palladium/carbon, platinum, Raney-nickel or the like as the catalyst, or by means of a complex metal hydride.

The compounds of formula III can also be prepared by reducing a compound represented by the formula

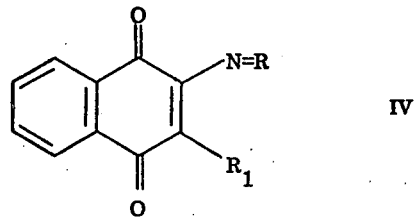

IV wherein R and R₁ have the significance given earlier.

The reduction of a compound of formula IV can be carried out in a conventional manner. Suitable reduction methods are, for example, catalytic hydrogenation using palladium, platinum, Raney-nickel or the like as the catalyst or reduction using a complex metal hydride such as lithium aluminum hydride, sodium borohydride, lithium borohydride or the like. Where R₁ in a compound of formula IV is halogen, this halogen can be split off during the catalytic hydrogenation. However, if desired, halogen at R₁ can be subsequently re-introduced in a conventional manner.

The compounds of formula IV are novel and are included in the present invention. Preferred compounds of formula IV are those wherein R₁ is halogen, preferably chlorine or bromine, most preferably wherein R₁ is chlorine.

The compounds of formula IV can be obtained by reacting a compound of formula II with cyclopentylimine or cycloheptylimine. This reaction is conveniently carried out in an inert organic solvent at a temperature from about room temperature to the reflux temperature of the reaction mixture.

EXAMPLE 1

18.7 G. of cyclopentylamine in 50 ml. of absolute ethanol are added dropwise while stirring at room temperature to a suspension of 22.7 g. of 2,3-dichloro-1,4-naphthoquinone in 100 ml. of absolute ethanol. After the addition, the mixture is boiled under reflux for 1 hour. The resulting dark-red mixture is then evaporated under reduced pressure. The residue is then dissolved in 600 ml. of chloroform and shaken out successively with 200 ml. of water, three times with 100 ml. of 3-N hydrochloric acid each time and three times with 100 ml. of water each time. After drying over sodium sulfate, the chloroform solution is concentrated, treated with active carbon and evaporated. After crystallization from n-hexane, 23.9 g. of 2-cyclopentylamino-3-chloro-1,4-naphthoquinone of melting

EXAMPLE 2

In a manner analogous to that described in Example 1, 2-cycloheptylamino3-chloro-1,4-naphthoquinone of melting point 97°–99°C. (from n-hexane) is obtained from 2,3-dichloro-1,4-naphthoquinone and cycloheptylamine.

EXAMPLE 3 a. 1.52 G of 2-cycloheptylamino-3-chloro-1,4-naphthoquinone are dissolved in 70 ml. of absolute ethanol and hydrogenated in the presence of 250 mg. of palladium/carbon (5%) at room temperature and normal pressure. After completion of the hydrogen uptake, the mixture is separated from the catalyst under nitrogen. The resulting solution is concentrated and the residue crystallized from methylene chloride. There is thus obtained 2-cycloheptylamino3-chloro-1,4-dihydroxynaphthalene of melting point 125°–127°C.

In a manner analogous to that described in paragraph (b) of this Example, 2-cyclopentylamino-3-chloro-1,4-naphthoquinone can be manufactured from 2-cyclopentylamino-3-chloro-1,4-dihydroxynaphthalene which is made in a manner analogous to that described in paragraph (a) of this Example.

b. 100 Mg. of 2-cycloheptylamino-3-chloro-1,4-dihydroxynaphthalene are dissolved in 20 ml. of absolute ethanol. Air is passed through the resulting solution for 30 minutes. The resulting red solution is subsequently evaporated in vacuo and the residue chromatographed on 20 g. of silica gel (0.2–0.5 mm.) using methylene chloride for the elution. 32 Fractions each of 10 ml. are collected. Fractions 18–29 contain the desired product, 2-cycloheptylamino-3-chloro-1,4-naphthoquinone. After evaporation of the solution, the product is crystallized from petroleum ether. It has a melting point of 98°–100°C.

EXAMPLE 4

Capsules containing the following ingredients are prepared in the usual manner:

| | |
|---|---|
| 2-Cycloheptylamino-3-chloro-1;4-naphthoquinone | 200 mg. |
| Lactose | 110 mg. |
| Maize starch | 35 mg. |
| Talc | 5 mg. |

EXAMPLE 5

Tablets of the following composition are prepared in the usual manner:

| | |
|---|---|
| 2-Cyclopentylamino-3-chloro-1,4-naphthoquinone | 100 mg. |
| Lactose | 50 mg. |
| Maize starch | 23 mg. |
| Calcium stearate | 2 mg. |

We claim:

1. A compound represented by the formula

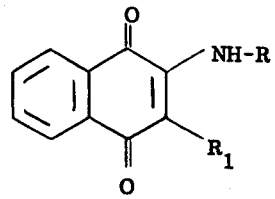

wherein R is cyclopentyl or cycloheptyl and $R_1$ is halogen or lower alkoxy.

2. The compound of claim 1 wherein R is cyclopentyl and $R_1$ is chlorine.

3. The compound of claim 1 wherein R is cycloheptyl and $R_1$ is chlorine.

* * * * *